United States Patent
Uutela (10) Patent No.: US 9,445,741 B2
(45) Date of Patent: Sep. 20, 2016

(54) SYSTEM AND METHOD FOR BEAMFORMING IN SOFT-FIELD TOMOGRAPHY

(75) Inventor: Kimmo Henrik Uutela, Helsinki (FI)

(73) Assignee: General Electric Company, Schenectady, NY (US)

( * ) Notice: Subject to any disclaimer, the term of this patent is extended or adjusted under 35 U.S.C. 154(b) by 322 days.

(21) Appl. No.: 13/285,822

(22) Filed: Oct. 31, 2011

(65) Prior Publication Data

US 2013/0109962 A1    May 2, 2013

(51) Int. Cl.
*A61B 5/053*    (2006.01)
*A61B 6/03*    (2006.01)

(52) U.S. Cl.
CPC .................................. *A61B 5/0536* (2013.01)

(58) Field of Classification Search
CPC ...................................................... A61B 5/0536
See application file for complete search history.

(56) References Cited

U.S. PATENT DOCUMENTS

| | | | |
|---|---|---|---|
| 4,977,896 A | 12/1990 | Robinson et al. | |
| 5,269,325 A | 12/1993 | Robinson et al. | |
| 2010/0198101 A1* | 8/2010 | Song et al. | 600/547 |
| 2011/0082383 A1* | 4/2011 | Cory et al. | 600/547 |
| 2012/0157817 A1* | 6/2012 | Tucker | 600/383 |

OTHER PUBLICATIONS

Polydorides., "Image Reconstruction Algorithms for Soft-Field Tomography". University of Manchester Institute of Science and Technology. 2002.*

Vauhkonen., "Electrical impedance tomography and prior information". Kuopio University Publications C. Natural and Environmental Sciences 62. 1997.*

Costa et al., "Model Fitting and Error Estimation". Systems Biology: Biomedical Modeling. Yale. Spring 2010.*

Kulkarni et al., "A two-layered forward model of tissue for electrical impedance tomography". Physiol. Meas. 30(6) 19-34. 2009.*

Lionheart, "EIT reconstruction algorithms: pitfalls, challenges and recent developments". Physiol. Meas. 25. 125. 2004.*

Jovicic et al., "Application of the maximum signal to interference ratio criterion to the adaptive microphone array", Acoustics Research Letters Online, vol. 6, No. 4, pp. 232-237, Oct. 2005.

* cited by examiner

*Primary Examiner* — Long V Le
*Assistant Examiner* — Colin T Sakamoto
(74) *Attorney, Agent, or Firm* — Dean D. Small; The Small Patent Law Group, LLC (57) ABSTRACT

A system and method for beamforming in soft-field tomography are provided. One soft-field tomography system includes a plurality of transducers configured for positioning proximate a surface of an object and one or more excitation drivers coupled to the plurality of transducers and configured to generate excitation signals for the plurality of transducers. The excitation signals include at least one frequency component. The soft-field tomography system further includes one or more response detectors coupled to the plurality of transducers and configured to measure a response of the object at the plurality of transducers to the excitation applied by the plurality of transducers based on the excitation signals. The soft-field tomography system also includes a soft-field reconstruction module configured to reconstruct a property distribution based on the excitation signals and the measured response using an Electrical Impedance Spectroscopy (EIS) beamformer.

8 Claims, 4 Drawing Sheets

SYSTEM AND METHOD FOR BEAMFORMING IN SOFT-FIELD TOMOGRAPHY

BACKGROUND

The subject matter disclosed herein relates generally to data reconstruction systems and methods, and more particularly to systems and methods to reconstruct data in soft-field tomography.

Soft-field tomography, such as Electrical Impedance Spectroscopy (EIS) (also referred to as Electrical Impedance Tomography (EIT)), diffuse optical tomography, elastography, and related modalities may be used to measure the internal properties of an object, such as the electrical properties of materials comprising internal structures of an object (e.g., a region of a human body). For example, in EIS systems, an estimate is made of the distribution of electrical conductivities of the internal structures. Such EIS systems reconstruct the conductivity and/or permittivity of the materials within the area or volume based on an applied excitation (e.g., current) and a measured response (e.g., voltage) typically acquired at a surface of the area or volume. Visual distributions of the estimates can then be formed.

In EIS, the complex conductivity distributions within a volume are determined using assumed known applied electrical excitations, apriori geometry and surface electrode data, and signal measurement data from transducers coupled to the volume under test. An electromagnetic model with assumptions about the volume and electrode geometry, boundary conditions, the applied excitation, and the interior conductivity distribution are then used to determine a predicted response to a given excitation. The inverse problem in EIS is to determine the spatial distribution of complex conductivities that give rise to the difference between measured data and the predicted model data.

The EIS inverse problem is highly ill-posed in that large perturbations in the conductivity distribution may result in small changes in the measurement data. Similarly, small changes or errors in the applied excitation may result in large changes in the measured data. In some applications, such as stroke detection, the signal-to-noise ratio may be too low to accurately identify the impedances.

Conventional EIS is performed using a single measurement or determining a difference between two measurements to provide reconstruction localization or image generation. However, in some environments, for example in a hospital environment, estimates of the temporal behavior of impedance changes over time can be useful, such as for patient monitoring.

BRIEF DESCRIPTION

In accordance with an embodiment, a soft-field tomography system is provided that includes a plurality of transducers configured for positioning proximate a surface of an object and one or more excitation drivers coupled to the plurality of transducers and configured to generate excitation signals for the plurality of transducers. The excitation signals include at least one frequency component. The soft-field tomography system further includes one or more response detectors coupled to the plurality of transducers and configured to measure a response of the object at the plurality of transducers to the excitation applied by the plurality of transducers based on the excitation signals. The soft-field tomography system also includes a soft-field reconstruction module configured to reconstruct a property distribution based on the excitation signals and the measured response using an Electrical Impedance Spectroscopy (EIS) beamformer.

In accordance with another embodiment, a method for Electrical Impedance Spectroscopy (EIS) is provided. The method includes determining approximate regions of interest in an object being interrogated by a soft-field tomography system and forward calculating voltage changes related to expected impedance changes measured by the soft-field tomography system. The method further includes measuring responses of the object to excitations applied by the soft-field tomography system, updating a correlation matrix and calculating a beamformer waveform using the measured responses. The method also includes determining an impedance waveform using a linear operator to determine a property distribution of the object.

In accordance with yet another embodiment, a computer readable storage medium for performing soft-field tomography and determining a property distribution of an object using a processor is provided. The computer readable storage medium includes instructions to command the processor to acquire excitation signals information and response information from a soft-field tomography system interrogating an object. The computer readable storage medium further includes instructions to command the processor to reconstruct a property distribution of the object based on the excitation signals and measured responses using an Electrical Impedance Spectroscopy (EIS) beamformer.

BRIEF DESCRIPTION OF THE DRAWINGS

The presently disclosed subject matter will be better understood from reading the following description of non-limiting embodiments, with reference to the attached drawings, wherein below.

DETAILED DESCRIPTION

The foregoing summary, as well as the following detailed description of certain embodiments, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors, controllers, circuits or memories) may be implemented in a single piece of hardware or multiple pieces of hardware. It should be understood that the various embodiments are not limited to the arrangements, component/element interconnections and instrumentality shown in the drawings.

As used herein, a module or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" a module or a plurality of modules having a particular property may include additional such modules not having that property.

Various embodiments provide a system and method for soft-field tomography, and more particularly, using beamforming in Electrical Impedance Spectroscopy (EIS) to determine impedances from a region of interest as a function of time. A technical effect of at least one embodiment is providing optimization for temporal EIS, for example, improved or optimal signal-to-noise ratio for estimating the impedance values within a region of interest (ROI) and enabling reliable classification of the tissue within the ROI (e.g., classification of hemorrhagic or ischemic stroke). Additionally, at least one other technical effect is providing linearity and/or flexibility in EIS.

It should be noted that although the various embodiments are described herein in connection with EIS, also referred to as Electrical Impedance Tomography (EIT), the various embodiments may be implemented in connection with other soft-field tomography systems, such as Diffuse Optical Tomography (DOT), Near InfraRed Spectroscopy (NIRS), thermography, elastography or microwave tomography, and related modalities. It also should be noted that as used herein, "soft-field tomography" refers generally to any tomographic or multidimensional extension of a tomographic method that is not "hard-field tomography".

Figure 1:
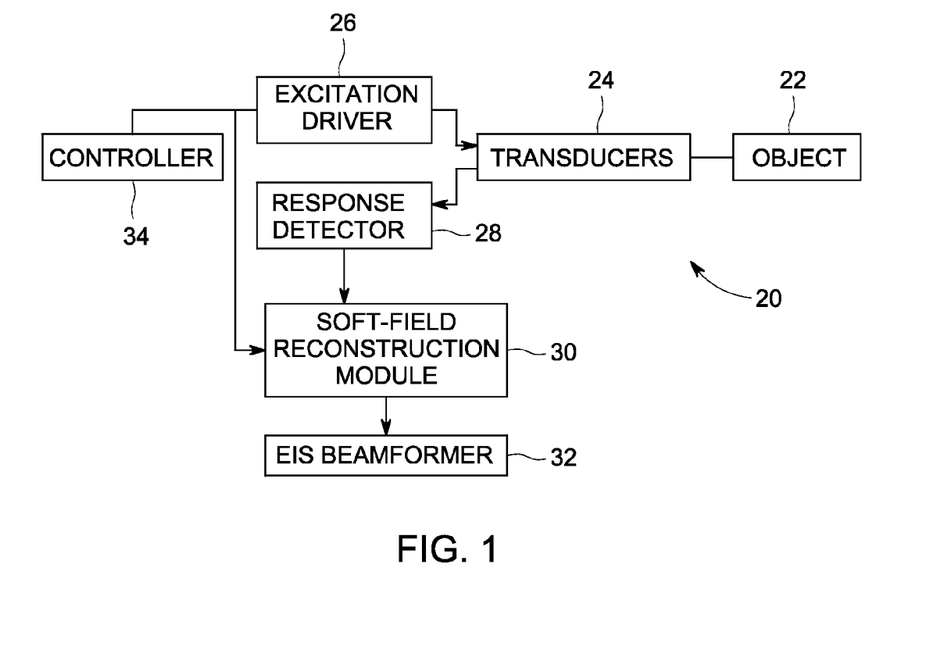
FIG. 1 is a simplified block diagram illustrating a soft-field tomography system formed in accordance with various embodiments.

One embodiment of a soft-field tomography system 20 is illustrated in FIG. 1. For example, the soft-field tomography system 20 may be an EIS system, also referred to as an EIT system used to determine the electrical properties of materials within an object 22 (e.g., a person) as illustrated in FIG. 1. For example, the spatial distribution of electrical conductivity (σ) and/or permittivity (ε) may be determined inside the object 22 or other area or volume. Thus, internal properties of the object 22 may be determined. In the illustrated embodiment, the system 20 includes a plurality of transducers 24 (e.g., electrodes) that are positioned at or proximate a surface of the object 22, which in a healthcare application (e.g., patient monitoring or tissue characterization) may include attaching the plurality of the transducers 24 to the skin of a patient or subject. For example, the transducers 24 may be positioned on the surface of the object 24 (e.g. electrodes, thermal sources, ultrasound transducers), near the surface of the object 24 (e.g., radiofrequency antenna), or penetrating the surface of the object 24 (e.g., needle electrodes). Thus, the transducers 24 may take different forms, such as surface-contacting electrodes, standoff electrodes, capacitively coupled electrodes, conducting coils, and antennas, among others.

An excitation driver 26 and a response detector 28 are coupled to the transducers 24, which are each connected to a soft-field reconstruction module 30. The soft-field reconstruction module 30 may be any type of processor or computing device that performs soft-field reconstruction based at least in part on received responses from the transducers 24 and performs EIS beamforming using an EIS beamformer 32 as described in more detail herein. The soft-field reconstruction module 30 may be hardware, software or a combination thereof. In one embodiment, the excitation driver 26 and the response detector 28 are physically separate devices. In other embodiments, the excitation driver 26 and the response detector 28 are physically integrated as one element. A controller 34 is also provided and sends instructions to the excitation driver 26 that drives the transducers 24 based on the instructions. It should be noted that an excitation driver 26 may be provided in connection with all of the transducers 24 or a subset of the transducers 24.

It also should be noted that different types of excitations may be used to obtain property distribution data for use in the reconstruction process. For example, electrical, magnetic, optical, thermal or ultrasound excitations, among others, may be used in combination with the various embodiments. In these different embodiments, the transducers 24 may be coupled to the object 22 in different ways and not necessarily in direct contact or only at a surface of the object 22 (e.g., coupled electrically, capacitively, galvanically, etc.).

In one embodiment, the object 22 is a human body region, such as a head, a chest, or a leg, wherein air, blood, muscle, fat, and other tissues have different electrical conductivities. The soft-field tomography system 20 estimates or determines conditions of the internal properties (e.g., material properties or the presence of blood) of the human body region, and thus can assist in the diagnoses or detection of diseases, for example, associated with hemorrhage, tumor, and lung function, among others. In one embodiment, the soft-field tomography system 20 is used for patient mentoring for stroke detection. For example, in some embodiments the soft-field tomography system 20 may be used for follow-up monitoring when a hemorrhage is possible or expected in a known area of the brain.

The object 22 is not limited to humans and animals are also subject to the techniques detailed herein. In other embodiments, the soft-field tomography system 20 can be used for generating a visual representation of the electrical impedance distribution in a variety of other applications, such as for determining the material properties in a mixed flow including oil and water, or for an underground earth area for soil analysis and roadbed inspection, among others.

In various embodiments, the transducers 24 are formed from any suitable material. For example, the types of transducer 24 used may be based on the particular application, such that a corresponding transducer type (e.g., electrode, coil, etc.) is used to generate the soft-field excitations (e.g., electromagnetic field) and receive responses of the object 22 to the excitations for the particular application. In some embodiments, a conductive material may be used to establish electrical current. For example, the transducers 24 may be formed from one or more metals such as copper, gold, platinum, steel, silver, and alloys thereof. Other exemplary materials for forming the transducers 24 include non-metals that are electrically conductive, such as a silicon based materials used in combination with micro-circuits. In one embodiment, where the object 22 is a human body region, the transducers 24 are formed from silver-silver chloride. Additionally, the transducers 24 may be formed in different shapes and/or sizes, for example, as rod-shaped, flat plate-shaped, or needle-shaped structures. It should be noted that in some embodiments, the transducers 24 are insulated from one another. In other embodiments, the transducers 24 can be positioned in direct ohmic contact with the object 22 or be capacitively coupled to the object 22.

In operation, the transducers 24 or a subset of the transducers 24 may be used to transmit signals (e.g., deliver or modulate signals), for example, deliver electrical current continuously or to deliver a time-varying signal such that excitations may be applied across a temporal or varying frequency range (e.g., 1 kHz to 1 MHz) to the object 22 to generate an electromagnetic (EM) field within the object 22. In an EIS or EIT application, the resulting surface potentials, namely the voltages on the transducers 24 are measured to determine an electrical conductivity or permittivity distribution using one or more suitable reconstruction methods, which includes signal beamforming in accordance with one or more embodiments. Accordingly, a visual distribution may be reconstructed based on the geometry of the transducers 24, the applied currents and the measured voltages.

Thus, in various embodiments, the excitation driver 26 applies an excitation to each of the transducers 24 and the response detector 28 measures a response of the object 22 at each of the transducers 24 (which may be multiplexed by a multiplexer) in response to the excitation applied on the transducers 24. It should be noted that any type of excitation may be provided, for example, electrical current, electrical voltage, a magnetic field, a radio-frequency wave, a thermal field, an optical signal, a mechanical deformation and an ultrasound signal, among others.

Figure 2:
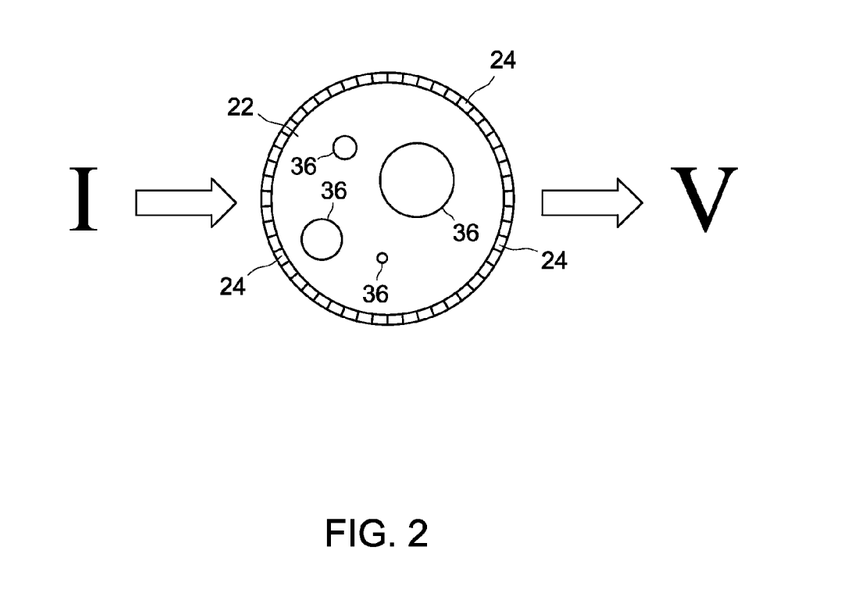
FIG. 2 is a simplified diagram illustrating reconstruction of a property distribution.

For example, in an EIS or EIT application, and as illustrated in FIG. 2, a soft-field reconstruction is performed to identify ROIs 36 (e.g., blood in the brain) within the object 22, which in various embodiments is to identify changes in the ROIs 36. As shown, the response detector 28 (shown in FIG. 1) measures a response voltage (or a response current) on the transducers 24 in response to the current (or voltage) applied by the excitation driver 26 (shown in FIG. 1) to the transducers 24. It should be noted that the ROIs 36 also may be initially located using other imaging modalities, for example, x-ray Computed Tomography (CT).

It should be noted that the response detector 28 also may include one or more analog-signal-conditioning elements (not shown) that amplifies and/or filters the measured response voltage or current. In other embodiments, a processor of the soft-field tomography system 20 includes a signal conditioning element for amplifying and/or filtering the response voltage or response current received from the response detector 28.

Figure 3:
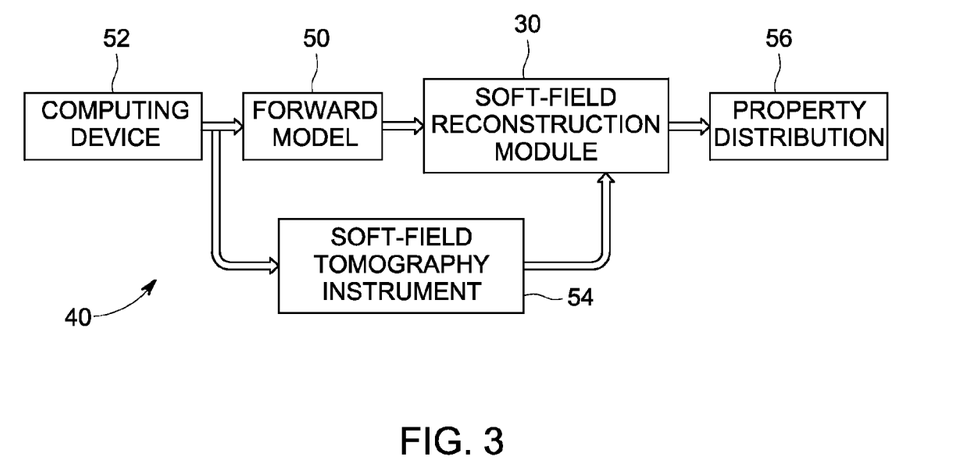
FIG. 3 is a block diagram illustrating soft-field tomography information flow in accordance with various embodiments.

The soft-field reconstruction module 30, thus, computes a response of the object 22 to the applied excitation. For example, an EIS information flow 40 is illustrated in FIG. 3. In particular, a forward model 50 is used based on excitations from a computing device 52, to predict voltages (predicted data), which are provided to the soft-field reconstruction module 30. In one embodiment, an inverse problem relating the measured responses (e.g., measured signals), the applied excitations, and the electrical conductivity distribution inside of the object 22 being tested or interrogated by the soft-field tomography system 20 is solved by the reconstruction module 30.

The excitations are applied to the object 22 (shown in FIGS. 1 and 2) by a soft-field tomography instrument 54, which may include the transducers 24 and other excitation and measurement components, and thereafter measured voltages (measured data) are communicated to the reconstruction module 30. The soft-field reconstruction module 30 then performs reconstruction, which includes using one or more embodiments of EIS beamforming, to generate an estimate of the property distribution 56, for example, the impedance distribution, to identify ROIs 36 within the object 22. It should be noted that the various components may be physically separate components or elements may be combined. For example, the soft-field reconstruction module 30 may form part of the soft-field tomography system 20 (as illustrated in FIG. 1).

Using various embodiments, soft-field reconstruction (with EIS beamforming) is provided that uses a linear operator, which in various embodiments is an optimal or optimized linear operator, to determine impedances from the ROIs 36 as a function of time. Thus, the soft-field tomography system 20 may be used, for example, to estimate the temporal behavior of impedance changes over time, such as to monitor a patient for stroke conditions.

Figure 4:
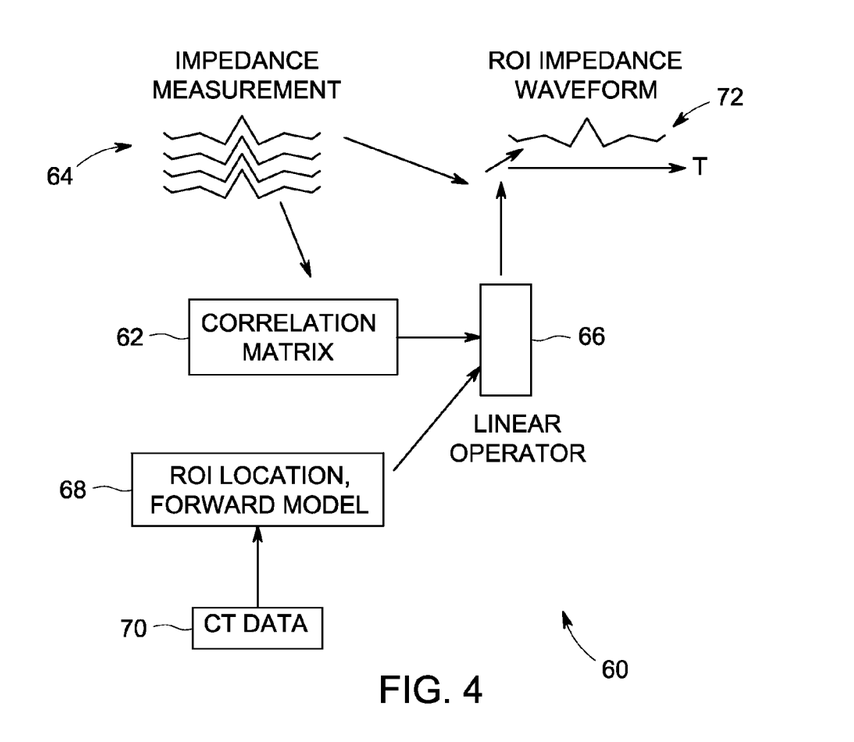
FIG. 4 is a block diagram of beamformer arrangement in accordance with various embodiments.

In one embodiment, a beamformer arrangement 60 may be provided as shown in FIG. 4. The beamformer arrangement 60 may be implemented in hardware, software, or a combination thereof and may be embodied, for example, as the EIS beamformer 32 (shown in FIG. 1). The beamformer arrangement 60 may be used in connection with the soft-field tomography system 20 to estimate impedance values within the ROIs 36 to allow for classification of the tissue within the areas defined by the ROIs 36. For example, in a stroke detection application, the various embodiments provide or facilitate the classification of hemorrhagic or ischemic stroke.

Figure 5:
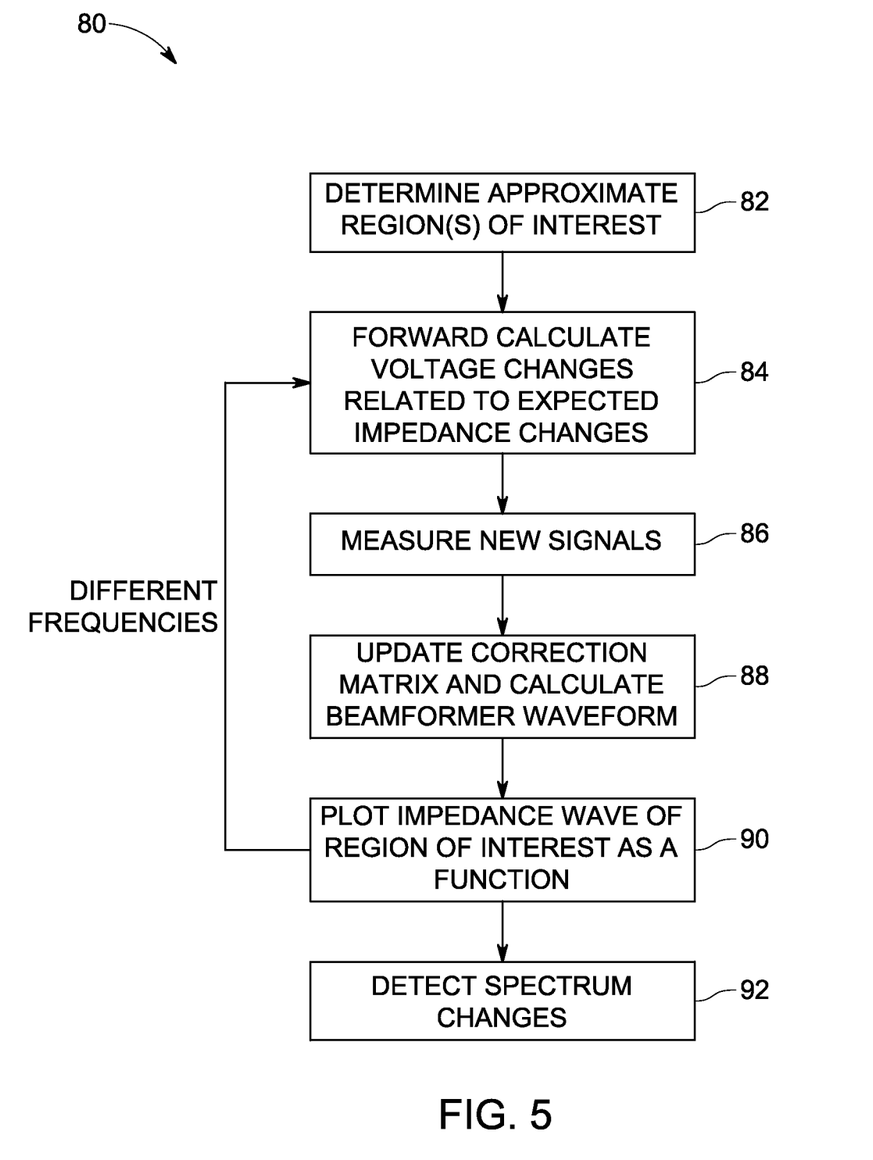
FIG. 5 is a flowchart of a method for Electrical Impedance Spectroscopy (EIS) beamforming in accordance with various embodiments.

The beamformer arrangement 60 will now be generally described with a more detailed description thereafter In connection with the flowchart 80 shown in FIG. 5. The beamformer arrangement 60 includes a correlation matrix 62 that is used to calculate a beamformer waveform based on impedance measurements 64, for example, as determined using the transducers 24 (shown in FIG. 1) and any suitable EIS measurement technique. The calculated beamformer waveforms are input to a linear operator 66. The linear operator 66, which in various embodiments is the EIS beamformer 32, also receives additional information 68, which includes location information (e.g., coarse location information) that generally approximates one or more ROIs 36 that may be determined, for example, from one or more different scans. In the illustrated embodiment, the location information is determined from computed tomography (CT) data 70, such as from one or more x-ray CT scans of a patient's head. For example, the CT data 70 may be used to determine the location of previous bleeding and/or a head trauma location. It should be noted that location information also may be determined retrospectively from impedance tomography results, such as from a previous EIS reconstruction. In a stroke application, the location information may identify the location of a small amount of blood in a particular area of the brain and also provide the general shape of the patient's head to define the boundaries for the EIS reconstruction.

The additional information 68 also includes forward calculated voltage changes related to expected impedance changes, such as calculated by the forward model 50 (shown in FIG. 3), which may be performed using any suitable EIS forward model technique. As described herein, the forward calculations may be performed by linearizing the relation at a set point corresponding to the baseline measurement.

It should be noted that the correlation matrix 62 may be updated offline or during monitoring based on the received impedance measurements 64. It also should be noted that the correlation matrix 62 is used to correlate the changes over time in the received signals with the changes due to location (e.g., movement of the patient) or noise removed using the known anatomy information, which in this embodiment is determined from the CT data 70. For example, using the known location of previous areas of interest or the shape/ boundary of the head, changes due to anatomy or noise may be subtracted out using any suitable subtraction technique.

The linear operator 66 uses the output from the correlation matrix 62 and the additional information 68 to perform beamforming as described in more detail below. For example, in various embodiments, the linear operator 66 is a weighting function (which in various embodiments is a linear operator) for different channels of the soft-field tomography system 20 (shown in FIG. 1), which may correspond to the number of transducers 24 (shown in FIG. 1).

Thus, in various embodiments, location information, which may be from an EIS reconstruction or a different scan (e.g., a CT scan) is used by the beamformer arrangement 60 in combination with EIS measurements, such as the impedance measurements 64 to generate an ROI impedance waveform 72, which represents impedances for the ROIs 36 as a function of time. Accordingly, the ROI impedance waveform 72 is a waveform that varies over time.

Is should be noted that the linear operator 66 also may provide current distributions that in various embodiments increases or maximizes the signal-to-noise ratio of the measurement of the regions of interest 36.

The beamformer arrangement 60 may perform EIS beamforming as illustrated in the flowchart 80 of FIG. 5, using one embodiment of EIS beamforming. The method 80 includes determining approximate ROIs at 82. For example, based on previous CT scans or EIS reconstructions, areas of interest in the brain of patients for potential stroke conditions are determined. The areas may include regions of interest based on previous bleeding and/or head trauma locations. Thereafter, voltage changes related to expected impedance changes are forward calculated at 84. For example, based on any suitable EIS model, one or more predicted responses (e.g., voltage changes) at one or more transducers may be determined as related to expected impedance changes from the application of excitations by the transducers. It should be noted that the forward calculating may include linearizing the system around a set point estimated from one or more previous measurements or responses. In particular, changes measured by the soft-field tomography system have a non-linear relation. Accordingly, in various embodiments the calculating may be performed by linearizing the relation at a set point corresponding to the baseline measurement.

Figure 6:
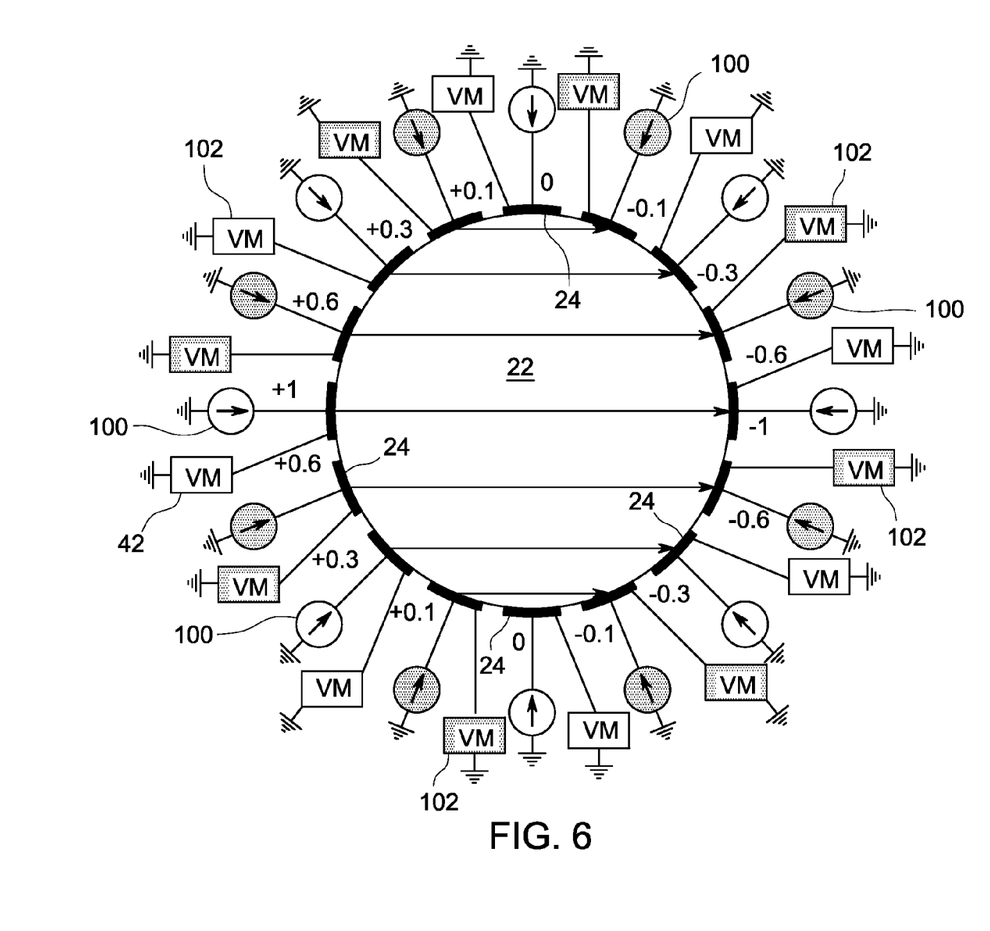
FIG. 6 is a simplified diagram illustrating one transducer configuration in accordance with various embodiments.

Thereafter, new signals are measured at 86. For example, in an EIS system, measured current responses to applied voltages at each of a plurality of transducers are measured. Any suitable soft-tomography method for generating responses for the internal structure of the object 22 (shown in FIG. 1) may be used, such as with a processor defining a geometry of the object 22, and discretizing the geometry into a structure having a plurality of nodes and elements. In one embodiment, as illustrated in FIG. 6, the excitation driver 26 applies an excitation on the geometry by providing an excitation, illustrated as an applied current 100, on each of the transducers 24 (e.g., electrodes), wherein the applied current 100 on each transducer 24 may be a single frequency or multi-frequency excitation signal. It should be noted that current and/or voltage sources may be provided, and may be more or less than the number illustrated. For example, each transducer 24, a set of the transducer 24 or all of the transducer 24 may share a current source or voltage source. The response detector 28 is illustrated as having a plurality of voltage measuring devices, such as voltmeters 102, for measuring a voltage at the electrodes 24. However, more or less voltmeters 102 or other measurement devices may be provided. It should be noted that the excitation and measured response (illustrated by the values around the periphery and by the arrows within the object 22) are simplified for illustration and the excitation and corresponding conductivity distribution may be more complex. Additionally, the illustrated values are again provided for simplicity and ease of understanding.

Referring again to FIG. 5, a correlation matrix (which may be initially formed based on previous EIS measurements) is updated at 88 and a beamformer waveform is also calculated. For example, based on signals (responses) measured at 86, the correlation matrix is updated, which is then used to calculate a beamformer waveform (e.g., a waveform over time). It should be noted that different matrix transformation based methods or algorithms may be used. For example, in one embodiment, the correlation matrix is a discrete Fourier transform (DFT) matrix that defines the distribution in a discrete matrix, such as for each transducer. For example, the correlation matrix may define the values for the applied and measured signals at each of the plurality of transducers.

Using a linearized model, which may include the linear operator 66, an impedance waveform, such as the ROI impedance waveform 72 is calculated, which may be plotted at 90 as a function over time for one or more ROIs. Thus, the impedance measurements, which may be measured current waveforms are transformed into an ROI impedance waveform over time using a linear operator that defines the beamforming as described in more detail herein.

It should be noted that steps 84, 86, 88 and 90 may be repeated for a plurality of different frequencies. For example, the ROI impedance waveform may be determined and plotted for measured responses resulting from excitations at different frequencies applied to the transducers.

Thereafter, spectrum changes are determined at 92, for example, having expected patterns or fingerprints. For example, using previously determined waveforms that correspond to material properties of interest (e.g., blood), a comparison may be performed or changes determined that correspond to the detection of blood, such as blood in the brain. It should be noted that the changes may be determined based on thresholding values.

With respect more particularly to the linear operator and EIS beamforming by the beamformer arrangement 60, such as using the method 80, a linearized model (from the impedance measurements) may be defined as follows:

$$\Delta u(t) = J \Delta z(t) + n(t) \qquad \text{Equation 1}$$

where $\Delta u(t)$ and $\Delta z(t)$ are vectors with voltage and impedance differences from a baseline, Jacobian J is du/dz at the baseline point, and n(t) is a noise and artifact vector.

In various embodiments, the linearization defined by Equation 1 may be used as an approximation for a stroke monitoring application to detect small impedance changes from the baseline. In particular, using the model defined by Equation 1, the contribution of an impedance change on the measured voltages is linear as follows:

$$\Delta u(t) = ax(t) + n(t) \qquad \text{Equation 2}$$

where a is the forward-calculated voltage change per unit change in the source impedance amplitude x(t). It should be noted that a is signal dependent, for example, based on the additional information 68 (shown in FIG. 4) from the other modality (e.g., CT), which is used to forward calculate the location of the regions of interest.

A beamformer vector w provides the estimated impedance change from the measured voltage difference as follows:

$$\hat{x}(t) = w\Delta u(t) \quad \text{Equation 3}$$

If the correlation matrix of n(t) is known, the signal-to-interference or signal-to-noise ratio (SNR) of x is:

$$SNR = \frac{w^t a E(x^2) a^t w^t}{w^t E(nn^t) w^t} \quad \text{Equation 4}$$

In various embodiments, maximizing Equation 4 produces an optimal beamformer.

In some embodiments, an estimated correlation matrix C(t) is used as the amount of data may not be sufficient for a reliable estimation. Accordingly, a regularized correlation matrix is combined from the estimate and the identity matrix, which results in:

$$\hat{w} = \frac{a^t(C(t) + \alpha I)^{-1}}{a^t(C(t) + \alpha I)^{-1} a} \quad \text{Equation 5}$$

where $\alpha$ is a regularization parameter and I is the identity matrix.

Equation 5 defines the linear operator 66 (shown in FIG. 4), which operates as the beamformer in the beamformer arrangement 60.

It should be noted that the regularization parameter a affects the resolution and noise level of the estimate. If a is very large, the beamformer reduces to a linear projection on the pattern vector, resulting in estimates that are not sensitive to uncorrelated noise, but are sensitive to impedance changes outside the region of interest, including artifacts. Thus, decreasing a results in an estimate that is more sensitive to the specific area, for example, the ROIs, but also sensitive to white noise.

Thus, using the linear operator 66, EIS beamforming is provided that allows for the calculation of impedances from ROIs as a function of times, as well to provide current distributions (e.g., excitation patterns) that increase or maximize the signal-to-noise ratio of the measurement of the regions of interest. In some embodiments, one or more excitation patterns for interrogating the object are selected to increase a speed of subsequent measurements of a region of interest (ROI), wherein the selecting is based on measurements with multiple excitations, forward calculations and/or a selection of the ROI as described herein. In various embodiments, based on the sensitivity information obtained when calculating the linear operator 66 for the waveform excitation(s), the excitation pattern(s) that are most relevant for a selected ROI are used in subsequent or future measurements.

The various embodiments and/or components, for example, the modules, elements, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as an optical disk drive, solid state disk drive (e.g., flash RAM), and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), application specific integrated circuits (ASICs), field-programmable gate arrays (FPGAs), graphical processing units (GPUs), logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program, which may form part of a tangible non-transitory computer readable medium or media. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software", "firmware" and "algorithm" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the invention without departing from their scope. While the dimensions and types of materials described herein are intended to define the parameters of the various embodiments of the invention, the embodiments are by no means limiting and are exemplary embodiments. Many other embodiments will be apparent to those of skill in the art upon reviewing the above description. The scope of the various embodiments of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments of the invention, including the best mode, and also to enable any person skilled in the art to practice the various embodiments of the invention, including making and using any devices or systems and performing any incorporated methods. The patentable scope of the various embodiments of the invention is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A method for Electrical Impedance Spectroscopy (EIS), the method comprising:

determining, using one or more processors, approximate locations of regions of interest in an object being interrogated by a soft-field tomography system;

predicting one or more predicted voltage changes related to expected impedance changes of the object based on an EIS model;

forward calculating, using the one or more processors, the one or more predicted voltage changes related to the expected impedance changes within the object from measured voltages by the soft-field tomography system, wherein the forward calculating comprises linearizing a system around a set point estimated from one or more previous measurements over time;

measuring, using the one or more processors, responses of the object to excitations applied by the soft-field tomography system;

updating, using the one or more processors, a correlation matrix using the measured responses, wherein the correlation matrix defines the excitations and measured responses of the soft-field tomography system and correlate the changes of the measured responses over time; and determining, using the one or more processors, an impedance waveform over time using a linear operator and the measured responses of the object to the excitations to determine a property distribution of the object, wherein the linear operator is calculated from the correlation matrix, the approximate locations of the regions of interest, and the forward calculated voltage changes.

2. The method of claim 1, further comprising determining, using the one or more processors, an impedance waveform for a plurality of different frequencies of excitations applied to the object.

3. The method of claim 1, wherein object is a person and the property distribution comprises blood in a brain of the person.

4. The method of claim 1, wherein the approximate locations of the regions of interest is based on x-ray computed tomography (CT) image data.

5. The method of claim 1, wherein the linear operator defines a weighting function as follows:

$$\hat{w} = \frac{a^t(C(t) + \alpha I)^{-1}}{a^t(C(t) + \alpha I)^{-1}a}$$

where a is a forward-calculated voltage change per unit change in a source impedance amplitude x(t), a is a regularization parameter, I is an identity matrix and C(t) is an estimated correlation matrix.

6. The method of claim 1, further comprising selecting, using the one or more processors, one or more excitation patterns for interrogating the object to increase a speed of subsequent measurements of a region of interest (ROI), the selecting based on measurements with multiple excitations, forward calculations and a selection of the ROI.

7. The method of claim 1, further comprising detecting one or more spectrum changes in the impedance waveform over time corresponding to the property distribution in the object.

8. The method of claim 1, wherein the correlation matrix is a discrete Fourier transform matrix that defines the distribution of a plurality of transducers of the soft-field tomography system.

* * * * *